(12) United States Patent
Johnston

(10) Patent No.: US 7,025,954 B2
(45) Date of Patent: Apr. 11, 2006

(54) MATERIALS FOR RESHAPING OF ESSENTIALLY RIGID KERATINACEOUS SURFACES

(75) Inventor: Allen D. Johnston, Linwood, PA (US)

(73) Assignee: Esstech, Inc., Linwood, PA (US)

( * ) Notice: Subject to any disclaimer, the term of this patent is extended or adjusted under 35 U.S.C. 154(b) by 355 days.

(21) Appl. No.: 10/151,590

(22) Filed: May 20, 2002

(65) Prior Publication Data
US 2003/0215635 A1 Nov. 20, 2003

(51) Int. Cl.
A61K 7/03 (2006.01)
C08F 2/50 (2006.01)

(52) U.S. Cl. .................. 424/61; 424/78.03; 522/81; 522/178; 522/179; 522/182; 522/65; 522/66; 522/104

(58) Field of Classification Search .......... 424/61, 424/78.03; 522/178, 179, 182, 65, 66, 68, 522/104, 107
See application file for complete search history.

(56) References Cited

U.S. PATENT DOCUMENTS

| | | | |
|---|---|---|---|
| 3,347,954 A | 10/1967 | Bredereck et al. | 260/864 |
| 4,209,604 A | 6/1980 | Werber | 526/270 |
| 4,288,221 A | 9/1981 | Engel | 433/202 |
| 4,387,240 A | 6/1983 | Berg | 556/440 |
| 4,413,108 A | 11/1983 | Janssen | 526/301 |
| 4,521,560 A | 6/1985 | Breitenfellner | 524/371 |
| 4,534,839 A | 8/1985 | Schaefer | 522/16 |
| 4,547,363 A | 10/1985 | Joos | 424/61 |
| 4,576,976 A | 3/1986 | Schaefer | 522/16 |
| 4,602,912 A | 7/1986 | de Sousa et al. | 8/127.5 |
| 4,766,005 A | 8/1988 | Montgomery et al. | 427/4 |
| 5,264,513 A | 11/1993 | Ikemura et al. | 526/318 |
| 5,290,172 A | 3/1994 | Sakuma et al. | 433/215 |
| 5,670,559 A | 9/1997 | Zeng et al. | 523/118 |
| 6,080,389 A | 6/2000 | Sheariss et al. | 424/61 |

FOREIGN PATENT DOCUMENTS

| | | |
|---|---|---|
| JP | 403182240 | 8/1991 |
| JP | 405186309 | 7/1993 |

*Primary Examiner*—Sanza L. McClendon
(74) *Attorney, Agent, or Firm*—Connolly Bove Lodge & Hutz

(57) ABSTRACT

In the disclosed method for the reshaping (adornment, repair, covering, prosthetic extension, etc.) of essentially rigid, keratinaceous surfaces such as nail plates with a free radical-polymerizable acrylic ester, the free radical initiator contains an encapsulated compound of the formula III (III)

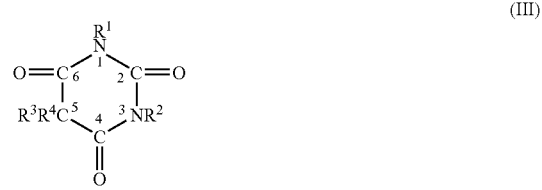

wherein $R^1$ through $R^4$ are identical to or different from each other and are hydrogen, a mononuclear carbocyclic aromatic group, a $C_1$–$C_{18}$ aliphatic group, a $C_1$–$C_{18}$ aliphatic radical substituted with a mononuclear carbocyclic aromatic group, a cycloaliphatic group or an aromatic radical having from 6 to 10 ring carbon atoms and up to five aliphatic or oxy- or oxo-aliphatic substituents, with the proviso that at least $R^3$ or $R^4$ is hydrogen. The compound of formula III, in chemically-curable systems is encapsulated into the polymer matrix and utilized in combination with a metal salt co-catalyst that is mixed with the polymer and, optionally, an organic buffering compound and a crosslinker.

21 Claims, No Drawings

MATERIALS FOR RESHAPING OF ESSENTIALLY RIGID KERATINACEOUS SURFACES

FIELD OF THE INVENTION

This invention relates to materials and methods for the reshaping (adornment, repair, covering, prosthetic extension, etc.) of human or animal, essentially rigid, keratinaceous surfaces. An aspect of this invention relates to materials and methods (e.g. two-part compositions) for a decorative, reparative, or prosthetic treatment, in vivo, of an essentially rigid, keratinaceous surface. An aspect of this invention relates to the formation of a solid, organic polymeric lamina in place on an essentially rigid keratinaceous surface. Still another aspect of this invention relates to the in-vivo reshaping of human nail plates (fingernails or toenails), using free radical-polymerizable materials.

DESCRIPTION OF THE PRIOR ART

The reshaping (repair, adornment, covering, prosthetic extension, etc.) of essentially rigid keratinaceous structures such as nail plates (human fingernails and toenails) and livestock hooves has been a common practice for centuries. This practice was greatly improved and facilitated by discoveries in the field of modern polymer chemistry. For example, it has been discovered that attractive and durable nail plate prostheses can be fashioned from curable acrylic systems (which could be chemically described as "acrylate esters" but are more typically referred to as "acrylic esters"), or curable acrylic systems blended with high molecular weight acrylic ester-type polymers. Foremost among these acrylics are the monomeric and/or polymeric acrylics wherein at least one polymerized and/or non-polymerized monomer is an acrylic ester, most typically an acrylic ester of the formula (I) R—OC(O)—C(R')=$CH_2$ (I) where R is an unsubstituted lower alkyl ($C_1$ to $C_6$) group or an alkyl group substituted with a hydroxy, carboxy, or lower alkoxy group, and R' is hydrogen or a lower alkyl group. A plurality of monomers (all of which are typically acrylic esters) can be used, and useful polymers include various copolymers (bipolymers, terpolymers, quaterpolymers, etc., most commonly two-unit random copolymers). In addition, a variety of techniques can be used, alone or in combination with acrylic systems, to improve the appearance or durability of nail plates. Nail plates can be coated with colored or clear nitrocellulose lacquer and repaired with cyanoacrylate adhesives as well as extended or otherwise reshaped with the aid of acrylic monomers and/or polymers.

Although the nitrocellulose lacquers and the cyanoacrylate adhesives are relatively adherent to nail plates and other essentially rigid keratinaceous surfaces, the acrylic esters and, more importantly, the polymers (including copolymers) obtained from them are not. Typically, adherence of an acrylic ester polymer to a nail plate is provided by a pre-treatment or adhesion-promotion treatment of the fingernail surface with an unsaturated monomer which can be an acrylic acid derivative such as methacrylic acid (current commercial embodiments containing in excess of 70 percent methacrylic acid). The acidic, monomeric adhesion promoter can, if desired be dissolved in a common liquid organic solvent (e.g. an aliphatic ketone or ester solvent or an aromatic, generally monocyclic, solvent). If adverse skin or nail reactions are encountered with acidic adhesion promoters or primers it may be desirable to utilize methods or formulate materials which lack this harshness. Non-acidic methods of improving adhesion to keratinaceous surfaces have been described in the patent literature; see U.S. Pat. No. 4,766,005 (Montgomery et al), issued Aug. 23, 1988. According to the Montgomery et al patent, the method of initiating the cure of the acrylic ester monomers is, however, conventional, e.g. an ultraviolet light cure or a "self-curing" (i.e. chemically initiated) system in which the initiator (catalyst/co catalyst) combination is benzoyl peroxide and a tertiary aromatic amine.

As disclosed in the Montgomery et al patent, similar technology can be used to repair the split or fractured hoof of an animal.

Acrylic ester monomers can be chain-extended and/or crosslinked with the aid of various catalyst systems or with the aid of radiant energy and a photoinitiator. For the treatment of essentially rigid keratinaceous surfaces such as nail plates, catalyst systems contained in the curable material are often preferred over photoinitiators, and the most commonly-used catalyst or chemical initiator system (which does not require radiant energy) is a two-part system made up of a peroxide and an amine. The peroxide is generally organic, e.g. benzoyl peroxide. Although benzoyl peroxide is an excellent free-radical initiator when used in combination with a tertiary aromatic amine co catalyst, non-aromatic (e.g. aliphatic) tertiary amines are far less effective in these catalyst systems. Unfortunately, the tertiary aromatic amine co catalysts have a tendency toward yellowing which can, with time, discolor a coating or prosthesis applied to a nail plate, unless the coating or nail plate is completely overcoated with a strongly colored lacquer. Thus, in the short term, the conventional benzoyl peroxide/aromatic amine initiator system is stable toward light, but in the long term, yellowing does occur. The yellowing problem is significant in the reshaping of nail plates, since, in the current practice of this technology, as much as 25% of the reshaping treatments are carried out without a complete overcoat or topcoat of strongly colored lacquer, either with no lacquering at all or with a clear topcoat or with a partial colored topcoat which leaves, for example, the tips of the prostheses exposed or clear-coated.

Moreover, the use of either benzoyl peroxide or an amine co catalyst (especially an aromatic tertiary amine) or the use of both in combination has created some concerns due to the toxicity of the substances and the possibility that they may be transported through skin or nail plates. Governmental agencies (e.g. in Europe) are presently considering stringent regulation or even outright prohibitions of the use of these peroxides and/or amine co catalysts in cosmetics.

When chemical initiator or catalyst systems not requiring radiant energy are employed, the most common method for reshaping (e.g. prosthetically extending) a nail plate is often referred to as the "powder/liquid" method. In this method, the keratinaceous surfaces (e.g. nail plates) are first washed and then primed or softened, then the "powder" and "liquid" are combined and applied. The "powder" comprises a particulate, chain-extended and/or crosslinked poly(acrylic ester) such as poly(ethyl methacrylate) or poly(ethyl acrylate)—which can, if desired be a suitable block or random copolymer, most typically a random ethyl/methyl acrylate or, more preferably, methacrylate copolymer.

The particles of polymer can be in the form of beads or tiny spheroids. The "liquid" typically comprises a monomer such as an acrylic ester, preferably an alkyl acrylate or alkyl alkylacrylate, the monomer being optionally dissolved in an organic liquid solvent. The powder and liquid are combined in the following manner. A shaping tool, which can be a brush, similar to an artist's paintbrush, is first dipped in a vessel containing the liquid monomer and then dipped in a vessel containing the powder. An doughy, adherent, agglomerated mass of particles is thus formed at the tip of the shaping tool (e.g. the brush). Alternatively, the powder can be slurried in the liquid to obtain a doughy mass, and the brush or other shaping tool is dipped in the dough. In either case the liquid monomer softens and partially dissolves the powder. The tip of the shaping tool, with its load of doughy material, is then used to sculpt a new nail shape or prosthesis, in place, on the existing nail plate.

In the powder/liquid system, the catalyst is in two parts, an organic peroxide component and an amine component. Typically, the organic peroxide has been blended with the powder, and the amine has been blended with the liquid monomer. When the powder and the liquid are combined, e.g. in the manner described above, the catalyst and co catalyst are also combined, and the free radical-initiated polymerization of the monomer can begin.

The yellowing effect created by the presence of an aromatic amine in the cured polymer is far less of a problem in light-curable systems. Typical photoinitiators such as camphorquinone, see, for example, U.S. Pat. No. 4,534,839 (Schaefer), issued Aug. 13, 1985, have a slight yellow color but tend to whiten under the influence of visible light, and, although aromatic tertiary amines are useful in camphorquinone-containing photocurable systems, aliphatic tertiary amines are equally if not more effective. Thus, the yellowing problem, while not entirely limited to the powder/liquid method for reshaping essentially rigid keratinaceous surfaces, is more strongly associated with that method. In any event, because of the toxicity problems associated with benzoyl peroxide/aromatic amine initiator systems, and because many users and consumers of nail-plate reshaping technology prefer the convenience of a completely chemical cure (sometimes called a "self cure"), the future of nail-plate reshaping technology now appears to be dependent upon finding an adequate substitute for this conventional free radical-initiating system.

The arts of free radical initiation, polymerization of acrylic monomers (especially acrylic ester monomers), and the treatment of nail plates are all highly developed. The following references are considered to be representative of the state of these arts: U.S. Pat. No. 4,766,005 (Montgomery et al, cited previously); U.S. Pat. No. 3,347,954 (Bredereck et al), issued Oct. 17, 1967; U.S. Pat. No. 4,288,221 (Engel), issued Sep. 8, 1981; U.S. Pat. No. 4,387,240 (Berg), issued Jun. 7, 1983; U.S. Pat. No. 4,547,363 (Joos), issued Oct. 15, 1985; U.S. Pat. No. 4,413,108 (Jansen), issued Nov. 1, 1983; U.S. Pat. No. 4,521,560 (Breitenfellner), issued Jun. 4, 1985; U.S. Pat. No. 4,534,839 (Schaefer), issued Aug. 13, 1985; and U.S. Pat. No. 4,576,976 (Schaefer), issued Mar. 18, 1986; U.S. Pat. No. 5,264,513 (Ikemura et al), issued Nov. 23, 1993. It has been found that compounds related to the barbiturates can be used in combination with synthetic pyrethroids to protect keratinaceous material from attack by pests; see U.S. Pat. No. 4,602,912 (de Sousa et al), issued Jul. 29, 1986.

Notwithstanding the progress made in these highly developed arts, there is still an urgent need for a method for reshaping (repairing, adorning, covering, prosthetically extending, etc.) essentially rigid keratinaceous surfaces which employs a catalyst or initiator system that does not necessarily require a radiant energy cure, is free of yellowing problems, and is low in toxicity.

SUMMARY OF THE INVENTION

It is has now been discovered by Sheariss et al. U.S. Pat. No. 6,080,389 issued June, 2000, that an extremely desirable catalyst system for reshaping essentially rigid keratinaceous surfaces can be formulated from a barbituric acid derivative and a co-catalyst comprising a metal salt. (Unsubstituted barbituric acid is theoretically operative, in that it is capable of forming a free radical, but it appears to have relatively low reactivity in this particular use environment, particularly as compared to barbituric acid derivatives.) In the powder/liquid system, the barbituric acid derivative is blended with the powder, and the metal salt co catalyst is blended with the liquid monomer. The catalyst or initiator systems of this invention do not require the presence of aromatic amines, and the improvement in color stability of uncoated prostheses or prostheses coated (in whole or in part) with light-colored or clear lacquers or polishes has far exceeded reasonable expectations. Uncoated prostheses made according to this invention have been rigorously tested by exposure to light (including ultraviolet light, e.g. in weatherometer tests) and have exhibited outstanding color stability.

It is the discovery of this patent that the barbituric acid derivative can be encapsulated into the polymer so that the copper salt can be included with the powder side of the powder/liquid mixture. The polymer itself insulates the barbituric acid from the copper elements. Upon addition of the liquid monomer to the powder, the barbituric acid is released to react with the copper and initiate polymerization of the monomer. The removal of the copper species from the liquid increases the number of liquids that can be used with the initiating system because the copper can react with some monomers leading to premature gelling of the liquid.

The compound barbituric acid has the structure of formula II

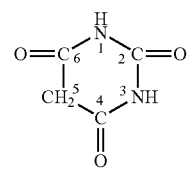

(II)

which allows at least for substitution at the 1-, 3-, and/or 5-positions, and substitution at these positions is particularly preferred over substitution at the 2-, 4-, and 6-positions, so that the three carbonyl groups do not have to be reduced or otherwise modified. (Although this invention is not bound by any theory, it is believed that the carbonyl groups may have a stabilizing effect upon free radicals.) The most preferred substitution patterns are 1,5 and 1,3,5, and 5 (3,5=1,5, since the compound is symmetrical), less preferably 1,3 (it is particularly preferred that one—or, less preferably, two—H-atom or H-atoms be available, presumably to facilitate free-radical formation, at the 5-position), and the preferred substituents either facilitate, or do not interfere with, polymerization, but, biologically speaking, are relatively inert. Thus, these substituents can be aliphatic (including arylaliphatic such as benzyl) and aromatic, particularly mononuclear or $C_6$-aromatic (e.g. phenyl, tolyl, and xylyl). Heteroaliphatic and heteroaromatic groups (e.g. oxa- and aza-aliphatic groups, pyridino groups, and the like) can be substituted on the barbituric acid nucleus, but aza-aliphatic and N-aromatic heterocycles are less preferred due to their amine-like properties. Cycloaliphatic radicals are less preferred from the standpoint of availability but can be used. Nitrogen- and sulfur-containing substituents such as amino groups, thiols, halogens, and the like are chemically operative but are more likely to have an adverse effect upon polymerization than, for example, hydrocarbyl substituents (groups which contain only carbon and hydrogen). Unsubstituted barbituric acid has a p$K_a$ of about 4 and hence can form salts, the alkali and alkaline earth metal salts being the best tolerated in biological environments. From the standpoint of maximizing the efficiency of polymerization, neither the free acid nor its salts are preferred over barbituric acid derivatives. The preferred barbituric acid derivatives have the formula III

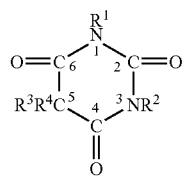

(III)

where $R^1$ through $R^4$ are hydrogen, mononuclear carbocyclic aromatic group, an aliphatic radical (preferably an aliphatic radical having up to 18 carbon atoms and including substituted aliphatic radicals), a $C_1$–$C_{18}$ aliphatic radical substituted with a mononuclear carbocyclic aromatic group, an aromatic radical having from 6 to 10 (preferably 6) ring carbon atoms and up to five aliphatic or oxy- or oxo-aliphatic substituents (e.g. alkoxides, esterified hydroxyls, or carbonyl-containing groups), or a cycloaliphatic radical (e.g. a five- or six-member carbocyclic or heterocyclic aliphatic group), or, less preferably, an amino group, a sulfhydryl group, a sulfhydryl salt group, or a halogen. The term "aliphatic" should be understood to include, in addition to lower alkyl groups and the like, arylaliphatic groups such as benzyl, although the benzyl group has a considerable amount of aromatic character due to the relatively minimal "insulating" effect of the methylene (—$CH_2$—) group which connects the ring position to the phenyl residue. Accordingly, the benzyl radical, which is one of the particularly preferred substituents, has both aromatic and aliphatic character and its inclusion within the genus "aliphatic" is for convenience of definition rather than for scientific classification. The phenylethylene radical has, by comparison, much less aromatic character, but is also useful in this invention and can be scientifically as well as definitionally classified as a substituted aliphatic radical.

Because barbituric acid itself is not preferred for use in this invention, it is particularly preferred that at least one of the groups $R^1$ through $R^4$ be a substituent other than hydrogen, but as indicated previously, one or two (more typically, but not essentially, just one) of the two radicals $R^3$ and $R^4$ is preferably hydrogen. The 1,3-disubstituted barbituric acid derivatives are operative in this invention, but they have been observed to have a tendency to be more sluggish in their reactivity as compared to 1,3,5-and 1,5-substituted derivatives.

The preferred aliphatic radicals—besides benzyl—are lower alkyl groups, including methyl, ethyl, propyl (isopropyl, n-propyl), butyl (n-butyl, i-butyl, sec-butyl, and t-butyl), and pentyl (or amyl). It is preferred that branched-chain alkyl radicals be substituted on the molecule in a manner that avoids steric hindrance problems, in the synthesis of the derivative and in its use, and 5,5-disubstitution can be detrimental to the catalytic or initiation activity of the barbituric acid derivative.

Barbituric acid derivatives used in this invention have some photoinitiation properties, see U.S. Pat. No. 4,576,976 (Schaefer), cited previously, but are preferably formulated for two-part or multi-part application as chemical ("self-curing") initiators. The photosensitizing properties of barbituric acid derivatives do not detract from their use in the powder/liquid method, described previously. Indeed, except for the use of the initiator system of this invention, the powder/liquid method of application can be carried out in essentially the conventional manner; that is, the catalyst system of this invention can simply take the place of the conventional organic peroxide/amine catalyst system and still meet all the demands of the powder/liquid method, while improving upon it in terms of low toxicity and color stability. The catalyst or initiator systems of this invention are extremely well tolerated in biological environments, including nail-plate and skin environments, especially as compared to the conventional organic peroxide/amine initiators.

The preferred metal salt co catalysts preferably meet the following criteria: first, they are preferably soluble in organic media such as common organic liquid solvents and, especially, in liquid, curable acrylic esters such as alkyl acrylates or alkyl alkylacrylates. Second, they should have at least two oxidation states besides the zero or metallic state (preferably positive or cationic states), and the energy difference between these states should be small, so that the salt can be converted from one oxidation state to the other with a small amount of energy input. Third, the salts should not produce stable, strongly colored species as a result of their cocatalytic (co-initiating) action. Preferred anions in these metal salts are therefore organic (i.e. derived from organic acids). Among the preferred organic anions are those which can themselves form free radicals or can act as free radical stabilizers or protectors, hence the presence of carbonyl groups, double bonds, and free radical-forming methylene groups can be very useful in this regard. Salts of Groups I-B, IV-A, V-B, VI-B, VII-B, and VIII of the Periodic Table of the elements can satisfy these criteria, particularly Cu and the transition metals V, Rh, Re, Mo, and, less preferably, Cr. Salts of these metals having inorganic anions are not preferred, e.g. because of poor compatibility in a typical acrylic system. The organic acids from which the organic anions are obtained can be sulfonic, phosphonic, or, especially, carboxylic acids, hence the anions can be sulfonates, phosphonates, carboxylates, naphthenoates, acetylacetonates, and the like. The organic diketone can be 2,4 pentanedione, napththenoate or acetylacetonate. The preferred metal salts are Cu(I) and Cu(II) salts, the Cu(II) state being preferred as the state in which the salt is added to the formulation (the Cu[I] can presumably form in situ during the initiation reaction). The metal salt is optionally but preferably combined with an a compound having buffering properties which is also soluble in organic media, particularly in liquid acrylic esters. Foremost among these buffering compounds are organic ammonium salts such as salts of the formula IV $R^5$ $R^6$ $R^7$ $R^8$ $N^+$ $X^-$ (IV) where $R^5$, $R^6$, $R^7$, and $R^8$ are the same or different and are $C_1$–$C_{30}$-aliphatic (including aliphatic groups substituted with an aromatic group), $C_3$–$C_{12}$-cycloaliphatic, or, less preferably, aromatic radicals, where from one to three (preferably zero to two) of the groups $R^5$ through $R^8$ can be hydrogen, and X is halide, preferably bromide or chloride, an aryl or alkyl sulfonate or phosphonate, or one equivalent of sulfate or phosphate per equivalent of nitrogen. Thus, the ammonium salt can be a quaternary ammonium compound such as a di(higher alkyl)di(lower alkyl)ammonium chloride or a mono(higher alkyl)tri(lower alkyl)ammonium chloride. (It is preferred that the organic ammonium salt have a high degree of lipophilic character, hence at least one of the organic groups substituted on the nitrogen is preferably a higher aliphatic group, i.e. a group having more than 6 carbon atoms.)

DETAILED DESCRIPTION

Throughout this application, the terms "cure", "polymerization", "chain extension and/or crosslinking", and "free-radical cure" are used substantially synonymously, as are the terms "catalyst" and "initiator", even if greater-than-catalytic amounts of the "catalyst" or "initiator" are used. Thus, an "initiating amount" of the initiator can include amounts up to and including stoichiometric quantities. The free-radical mechanism for curing or polymerizing acrylic ester monomers is well understood and fully elucidated in the scientific literature, and need not be discussed in this application.

The free-radical initiation system or catalyst/co catalyst system is a key aspect of this invention and is described in greater detail below.

I. The Barbituric Acid or Barbituric Acid Derivatives

Barbituric acid (hereafter referred to as "BA") is also known as 2,4,6 (1H,3H,5H) pyrimidine trione or as malonurea or as 2,4,6-trioxohexahydropyrimidine. It can be prepared from, for example, hydurilic acid and nitric acid or from ethyl malonate and urea using a strong base (e.g. sodium ethoxide) as a condensing agent. In its unsubstituted form, BA has no hypnotic or sedative activity and is not a controlled substance. The most well-known of the controlled substances derived from BA are 5-substituted, especially 5,5-disubstituted, BA derivatives, e.g. the 5,5-di(lower alkyl)BA's. These 5,5-disubstituted compounds are, at best, sluggish and, at worst, inoperative as initiators and hence are not preferred for use in this invention. Moreover, the 5,5-BA derivatives are more likely to be controlled substances and hence inconvenient to use for that reason alone.

The preferred BA derivatives have been described above. Especially preferred derivatives are substituted with alkyl groups, α-aryl-alkyl groups (e.g. benzyl, 2-phenyl-ethyl, etc.), and monocarbocyclic aromatic groups (e.g. phenyl, tolyl, xylyl, etc.), or, less preferably from an availability standpoint, cycloalkyl groups (cyclopentyl, cyclohexyl, etc.). Lower alkyl (e.g. $C_1$–$C_6$-alkyl)-substituted derivatives are also preferred from an availability standpoint, but higher alkyl groups (e.g. groups having up to 18, more typically up to 12 carbon atoms) do riot detract from compatibility with the components of the acrylic polymers and curable acrylic ester materials used in this invention. The most preferred substituents for substituted BA's are thus lower alkyl (e.g. methyl), monocyclic aromatic (e.g. phenyl), and benzyl. Representative examples of such substituted BA's have the following substitution patterns, where lower alkyl groups and aryl groups can be the same or different: 1,3-di(lower alkyl); 1-(lower alkyl); 1,3-diaryl; 1,5-di(lower alkyl); 1,5-diaryl; 1-aryl, 5-(lower alkyl); 1-(lower alkyl), 5-aryl; 5-cycloalkyl; 5-(lower alkyl); 5-aryl; 5-benzyl; 1,3,5-tri (lower alkyl); 1,3-di(lower alkyl) 5-cycloalkyl; 1,3-di(lower alkyl) 5-aryl; 1-benzyl, 5-aryl; 1-aryl, 5-benzyl; 1-cycloalkyl; 3-(lower alkyl),5-aryl; 3-aryl, 5-(lower alkyl); 1,3,5-(triaryl); 1-aryl, 5-(lower alkyl); 1-(lower alkyl), 5-aryl; 1,3,5-tribenzyl; and, less preferably, BA derivatives substituted only at the 3-position.

Although BA or BA derivatives have photosensitizing properties and, in combination with a suitable metal salt, are effective chemical initiators, and although some organic peroxide initiators are effective in very small amounts, relatively larger amounts of BA or BA derivative (up to and including stoichiometric amounts) are preferably employed in this invention. In view of the essential exclusion, from compositions used in this invention, of inorganic fillers and pigments which can mask color changes, the relatively large amount of BA or BA derivative remaining in the poly (acrylic ester) after the completion of curing has added to the difficulty of predicting the degree of color stability obtainable with curable systems of this invention.

Fortunately, however, it has been found that even the clearest of cured compositions used in this invention have excellent color stability.

It is preferred that the BA derivative be essentially uniformly distributed throughout a mass of particulate solid acrylic polymer (most typically in bead form), e.g in the amount of about 0.1 to 10 parts per hundred parts of powder (0.1–10 phr), more typically 0.5 to 5 phr. The BA derivative is introduced to the polymer as an additive to the monomer before it is polymerized. The BA derivative is encapsulated into the beads of polymer.

Prior art researchers and practitioners have obtained a considerable amount of experience with BA and BA derivatives as chemical initiators and/or photosensitizers in connection with, for example, dental adhesives and dental restorative materials, especially as primers for these materials, wherein the substrate is vital hard tissue such tooth enamel or dentin. See, for example, U.S. Pat. No. 5,264,513 (Ikemura et al), issued Nov. 23, 1993 and the Schaefer patent (U.S. Pat. No. 4,534,839), cited previously. When a light cure is desired in the context of the present invention, the relatively modest visible-light photoinitiating properties of BA and its derivatives can be enhanced by using the BA or BA derivative in combination with a conventional photoinitiator, preferably free of aromatic amine groups, which is effective with radiant energy in the visible light range, i.e. at wavelengths of at least about 400 nanometers (nm). The preferred photoinitiator is camphorquinone, which is highly effective at wavelengths above 460 nm, but other photoinitiators can be used with proper precautions, e.g. of the aromatic ketone type, such as the benozoins, acetophenones, aromatic diketones or their ketalized derivatives, alone or in combination with amine accelerators which are preferably aliphatic amines (especially tertiary amines such as the trialkyl amines, including those trialkyl amines in which one or more alkyl groups can be OH-substituted, preferably on the carbon atom most remote from the C—N bond).

Prior art experience extends to the use of BA derivatives in combination with metal salt catalysts such $Cu(OCOR^a)_2$, where the —$OCOR^a$ group is the residue of an aliphatic or aromatic carboxylic acid such as a naphthenoate or acetyl acetonate group. See the Bredereck et al patent, cited previously.

Through the use of BA or, preferably, BA derivatives in accordance with the principles of this invention, organic peroxides (especially benzoyl peroxide) and aromatic amines can be excluded from both light-curable and chemically curable acrylic ester compositions, both one-part and two-part, so that these one-part or two-part systems are essentially free of these sources or potential sources of toxicity or yellowing. ("Essentially free" means that trace quantities or even larger quantities having essentially no toxic or yellowing effects can be present, although it is preferred to exclude organic peroxides and aromatic amines altogether.) In order for a peroxide such as benzoyl peroxide to be completely excluded from a polymerized acrylic powder used in this invention (e.g. a powder for the powder/ liquid method of reshaping nail plates, i.e. a poly[acrylic ester]), it is necessary to prepare the poly(acrylic ester) powder with an initiator other than the compound to be excluded, because small residual amounts (typically less than about 2 weight-%, preferably <1 weight-% of the powder) will remain in the acrylic polymer, and their removal from the powder can impose a serious cost burden upon the composition. On the other hand, so long as the presence of small amounts of peroxide is permissible from a toxicity standpoint, it is technologically unnecessary to remove this residual peroxide; it is far more important to exclude or minimize the content of tertiary aromatic amine. If amine accelerators are included in compositions employed in accordance with invention, they can be aliphatic or cycloaliphatic amines. If organic solvent-soluble or acrylic ester-soluble buffering compounds are employed, they can be protonated or quaternized aliphatic or cycloaliphatic amines, including aliphatic and cycloaliphatic amines in which the aliphatic or cycloaliphatic group or groups is or are hydroxy-, alkoxy-, amido-, or ester-substituted.

Surprisingly, a very small amount (e.g. less than about 2 weight-%) of aromatic and/or aliphatic acyl peroxide (e.g. benzoyl peroxide)—which can either be residual peroxide in the acrylic polymer powder or a further component deliberately added to the powder or the liquid—can assist in the curing of an acrylic monomer component used in a composition of this invention, even though no amine of any kind (or, at least, no aromatic tertiary amine) be present. Although this invention is not bound by any theory, it is believed that the BA-derivative/metal salt reaction generates a sufficient exotherm to raise the organic acyl peroxide up to or above its 10 hour half-life temperature.

Because camphorquinone is sensitive to visible light, one-part systems comprising BA or a BA derivative, camphorquinone, and, optionally, an amine accelerator, are preferably shielded from light, e.g. in sealed, opaque packages.

Although this invention is not bound by any theory, it is presently believed that BA or, preferably, a BA derivative, in both light-curable and chemically curable systems, acts, at least initially, as a reducing agent or electron-donating agent and probably can form a free radical, apparently with an assist from the metal salt, thereby initiating the cure of an acrylic monomer.

In chemically curable systems, it is believed that the BA or, preferably, the BA derivative can participate, with the aid of the metal salt, in propagation reactions.

II. Co Catalysts for Chemical Initiators

In two-part or multi-part, chemically curable systems, especially those adapted for use in the powder/liquid method of this invention, the dough or slurry or adherent mass of polymer particles is obtained from a polymer (including any copolymer) of an acrylic ester (e.g. an alkyl acrylate or alkyl alkylacrylate) which encapsulates the BA or, preferably the BA derivative and contains the metal salt co catalyst and a liquid comprising an acrylic ester monomer (including monomer mixtures) which and, optionally, the organic buffering compound. The dough or slurry is formed in the conventional manner and is sculpted in place on a nail plate or other essentially rigid keratinaceous surface in the conventional manner also.

In chemical (non-photosensitizing) initiator systems, the BA derivative and the metal salt co catalyst are isolated from each other by the encapsulating barrier of polymer until the method of application to the keratinaceous surface is begun. The dissolution of the polymer bead frees the BA or preferably the BA derivative to react with the metal salt.

As explained above, it is believed that the BA or BA derivative functions initially as a reducing agent and/or free radical-forming compound and also participates, along with the metal salt, in the propagation of the free radical-initiated polymerization of the acrylic ester monomer, also accepts electrons. The metal salt of the co catalyst can be present in catalytic quantities (e.g. <200 parts per million, preferably <100 ppm, based on the amount of liquid, curable acrylic ester monomer) and is selected to include metals having a plurality of positive oxidation states, preferably oxidation states which differ from each other in electrochemical potential by less than about a volt. It is particularly preferred that the metal of the metal salt be able to satisfy the condition $$|E°(M^{+n}/M^{+(n-m)})|<0.8 \text{ volt, preferably} <0.6 \text{ volt,}$$

where n is a number from 2 to 8, and m is $\geq 1$, e.g. from 1 to 5, and $|E°|$ is the absolute value of the electrode potential, i.e. the value regardless of sign. It is convenient, but not essential, to select salts in which the sign of the E° value is positive, in which case the electrode potential can be expressed without the absolute value symbol, i.e.:

$$E°(M^{+n}/M^{+(n-m)})<0.8 \text{ volt, preferably} <0.6 \text{ volt,}$$

where n and m are as defined above. A salt of a metal which satisfies the first of the above two E° equations but not the second can be selected for use in this invention, particularly when the E° is relatively low, as in the case of the $V^{+3}/V^{+2}$ electrode potential, which is only −0.2, and certain Cr(VI)/Cr(III) potentials, which are even lower (e.g. −0.12).

Copper salts are optimum choices in view of the fact that the electrode potential for $Cu^{+2}/Cu^{+1}$ is less than 0.2 volt and is also positive. Moreover, in the case of copper salts of the formula $CuOCOR^a$ and $Cu(OCOR^a)_2$, where $R^a$ is aliphatic (including oxy- or acetyl-substituted aliphatic) or aromatic, the copper salt, either alone or, if complexing occurs, in a complex with BA or a BA derivative, has no discoloration effects, notwithstanding the fact that there are inorganic copper compounds which are red, black, or other strong colors. After the acrylic ester has been polymerized in place on a nail plate, the copper salt remaining in the polymerized material continues to be remarkably free of discoloration effects. Even though the BA derivative/Cu(II) salt initiator system was first developed partly to avoid discoloration effects (see U.S. Pat. No. 3,347,954), the degree of color stability could not have been foreseen from prior art experience with dental adhesives and restorative compositions, since these compositions are usually either hidden from view or highly loaded with fillers and pigments which absorb or reflect light more or less uniformly throughout the visible spectrum and thus could be expected to mask discoloration effects. Masking of this type cannot be employed in the present invention, particularly when a nail plate prosthesis is wholly or partially uncoated or given a clear topcoat. Moreover, when clear topcoats are used, they can be essentially free of light (e.g. ultraviolet) absorbing compounds.

In the course of a redox reaction, the pH of a medium containing the metal salt can vary. Although this invention is not bound by any theory, it is believed to be beneficial to keep the pH of the salt-containing medium within controlled limits by including a buffering compound which is soluble in the medium, e.g. in acrylic esters and/or in common organic liquid solvents. The organic ammonium salts preferred for this purpose have been described previously, the most preferred of these salts having at least one, preferably two or three, higher alkyl groups (e.g. $C_8$–$C_{0.30}$-alkyl) and up to two or three lower alkyl groups, substituted on the nitrogen of the ammonium compound. Up to three hydrogens can be substituted on the nitrogen of the ammonium compound (as in cations of the formula $RNH_3^+$), but two hydrogens or less are preferred, hence quaternatry ammonium salts are especially preferred. The amount of ammonium salt can be small in relation to the amount of acrylic monomer, e.g. 0.1 to 5 phr.

III. Auxiliary Photoinitiators and One-Part Systems

The photoinitiators and accelerators which can be included with the BA or BA derivative to enhance light cures (light-induced generation of free radicals) have been described previously, the preferred photoinitiators being those which are effective at wavelengths of at least about 400 nm, e.g. camphorquinone. Although two-part systems can be formulated, wherein the BA derivative is isolated from light-cure accelerators and/or auxiliary photoinitiators, it is convenient in this embodiment of the invention to employ a one-part system which is shielded from light. The one-part photoinitiator can be included, for example, in powdered poly(acrylic ester) or in a liquid monomer.

IV. Acrylic Esters, Poly(Acrylic Esters), and Crosslinkers

Free radical-polymerizable acrylic esters used as liquid monomers in this invention are liquid at normal ambient temperatures and pressures (e.g. 20 to 25° C., at normal atmospheric pressure) and are polymerizable at temperatures in, for example, the range of 15 to 30° C. The most preferred acrylic esters are those of the formula

R—OC(O)—C(R'=C$_2$)    (I)

where R is a lower alkyl ($C_1$ to $C_6$) group (which can be unsubstituted or substituted, preferably substituted with a hydroxy, carboxy, or lower alkoxy group) and R' is hydrogen or a lower alkyl group. As explained previously, a plurality of these acrylic esters can be used as the light-curable material or as the liquid component in the powder/liquid method. The acrylic ester can be employed essentially solvent-free or dissolved in common organic liquid solvents such as lower aliphatic carboxylic esters, lower aliphatic ketones, monocyclic aromatic compounds, and the like. Generally clear or translucent liquids, essentially free of fillers, pigments, and other solid particulate (especially inorganic) matter are preferred.

Preservatives such as butylated hydroxy toluene can be included in one- or two-part systems used in this invention, but are not required and are ordinarily not included. Similarly, in two-part systems, the slurries or doughy masses obtained when the two parts are combined are also preferably essentially free of fillers, pigments, and particulate inorganic matter and should also be essentially free of organic peroxides and aromatic amines. (Trace amounts of these fillers and pigments can be present, but not enough to provide any masking effects.)

Of the acrylic esters which include functional groups other than the ester linkage and the double bond of formula (I), i.e. those in which R is a substituted alkyl group, the most preferred monomers are hydroxyalkyl-methacrylates or -ethacrylates such as 2-hydroxyethylmethacrylate and the hydroxypropylalkylacrylates. These monomers can be used alone or in combination with acrylic esters such as ethyl methacrylate or methyl methacrylate. The monomers in which $R^1$ is hydrogen are operative but generally not preferred.

After polymerization, the acrylic ester or acrylic esters form a polymer (homopolymer or copolymer), i.e. a poly(acrylic ester), e.g. poly(ethyl acrylate) or poly(methyl methacrylate) or poly(ethyl methacrylate) or poly(ethyl methacrylate/methyl methacrylate) or a similar homopolymer or copolymer (including terpolymers, quaterpolymers, etc.) which need not be linear and, typically, are crosslinked to some degree. Both chemical curing and photo-curing can produce crosslinked polymers which tend to resist attack by organic solvents.

Chemical crosslinkers are preferably included in "self-curing" two-part compositions, the most preferred of these crosslinkers being di-, tri-, or tetra-alkylacrylates. These crosslinkers are typically reaction products of the components comprising a polyol (glycol, triol, tetrol, etc.) and an alkylacrylic acid such as methacrylic acid, e.g. ethyleneglycol dimethacrylate. Typical glycols include lower alkylene glycols which can have repeating units, as in the case of diethylene glycol, triethylene glycol, etc.

V. Part A/Part B Systems and Kits

In a preferred embodiment of the method of this invention, the overall composition used to reshape nail plates or form an essentially rigid lamina on the surface of the nail plate provides a curable slurry or dough-like mass when mixed, e.g. by dipping a shaping tool such as a brush applicator into a powder component and into a liquid component. As indicated previously, both powder and liquid components are essentially free of organic peroxides (especially benzoyl peroxide) and aromatic amines. Thus, the overall composition referred to above is divided into isolated parts, preferably by packaging these parts separately. In a typical part A/part B system, the parts are:

A. a powdery mass comprising a poly(acrylic ester) with an encapsulated compound of the formula III

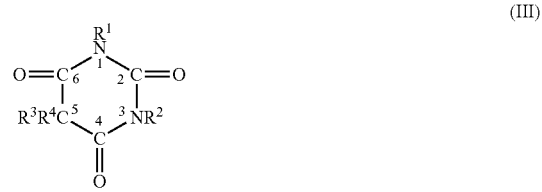

(III)

wherein $R^1$ through $R^4$ are hydrogen, an aliphatic group, an aromatic group, a cycloaliphatic group, or, less preferably, a sulfhydryl group, an alkali or alkaline earth metal salt of a sulfhydryl group, a halogen, or amino group; or $R^3$ or $R^4$ can be an alkali metal or alkaline earth metal cation when the 5-carbon is negatively charged;

B. a liquid acrylic ester monomer, containing a metal salt, preferably a reducible metal salt of a metal having a plurality of positive oxidation states, e.g. a copper (II) salt and, optionally, an organic buffering compound such as an organic ammonium salt; if a crosslinking compound such as a glycol dimethacrylate (bis-glycolmethacrylate) is included, dissolving this compound in the "B" part is an especially appropriate way to introduce it.

In this embodiment of the invention, a kit for use by a skilled cosmetic technician can be prepared by utilizing packages or containers for parts A and B which are sealed prior to use but when opened can provide ready access to the material in the container or package with a shaping tool. With regard to part B, it is preferred to dispense the monomer from a container with a closure having a spring-loaded or flexible portion which, when depressed, releases liquid. A suitable shaping tool (e.g. a paint brush) adapted to form or sculpt a nail plate prosthesis is preferably included in the kit. The shaping tool is preferably reuseable and can be cleaned by immersing the tip in organic solvent or liquid monomer.

Parts A and B are preferably formulated to be as simple as possible. Even ingredients such as solvents and diluents can be, and preferably are, excluded, as are insoluble inorganic materials and toxic or potentially toxic substances and substances which can cause discoloration of a poly(acrylic ester). As noted previously, preservatives and the like are entirely optional and can be omitted.

Optionally, the kit can include a nail polish or lacquer or topcoat material, which can be either colored or clear. Light (e.g. u.v.) absorbing compounds do not need to be included in the polish or lacquer or topcoat material, since the initiator systems of this invention are essentially free of aromatic amines and other compounds which can cause yellowing when exposed to light.

VI. Peroxide-Containing Compositions and Kits

In further embodiments of this invention, which can be in the form of a light-curable, or, more preferably, a chemically-curable (e.g. Part A/Part B) composition or kit material, organic peroxide is not completely excluded, although it is preferably present in a relatively small amount (e.g. less than about 2, more preferably <1, weight-%, most typically based on the weight of the powder component of a powder/liquid system). It is however preferred, in these embodiments, that the composition components be essentially free of any aromatic tertiary amine. The preferred route for introducing the organic peroxide (e.g. an aromatic acyl peroxide such as benzoyl peroxide) is to prepare the poly(acrylic ester) component of the composition or kit with the aid of a peroxide initiator. The residual organic peroxide remaining after the formation of the acrylic powder is sufficient to provide useful free-radical initiation effects later on, when the liquid acrylic monomer is cured in place on the keratinaceous surface. Deliberate introduction of organic peroxide into a previously cured acrylic powder or into an acrylic monomer is less preferred, since it adds an unnecessary step to the method for preparing a one-part or two-part system or an unnecessary modification of an existing step.

Thus, no amine co catalyst is needed to enable the organic peroxides to function as a second initiator, so to speak. The amount of metal salt co catalyst used in peroxide-free embodiments of this invention does not need to be modified for the peroxide-containing embodiments.

If health and safety laws or regulations do not prohibit the use of aromatic acyl peroxides in cosmetics, these peroxide-containing embodiments can be advantageous. The amount of peroxide is generally too small to create significant toxicity hazards, and the ability of the peroxide to assist in a free-radical cure is, surprisingly, largely unaffected by the exclusion of tertiary aromatic amine (hence, if desired, the aromatic tertiary amine can be fully excluded). As a result, the peroxide-containing embodiments provide a somewhat improved cure without the risk of yellowing discussed previously.

Among organic peroxides, unsubstituted or substituted benzoyl peroxides

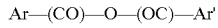

Ar—(CO)—O—(OC)—Ar' wherein Ar and Ar' are the same or different and are aromatic groups (preferably having only one ring) are especially preferred for their long half life at normal ambient temperatures and their solubility characteristics; a further desirable property of benzoyl peroxide is the modest temperature of its 10 hour half-life.

However, other organic acyl peroxides have similar properties including those of the formula $R^{10}$—(CO)—O—O—(OC)—$R^{11}$, where $R^{10}$ and $R^{11}$ are $C_1$–$C_{18}$-aliphatic and/or $C_6$–$C_{14}$ aromatic, a typical example of such other peroxides being t-butyl peroctoate, which has been used in free radical initiation because of a 10 hour half-life temperature which is similar to that of benzoyl peroxide. Preferred organic acyl peroxides used in this embodiment of this invention have a 10 hour half-life temperature of at least 30 ° C., preferably at least 40 to 50 ° C. Ten hour half-life temperatures >70° C. are operative, but not preferred, since the inherent thermal insulating effect of a nail plate is most effective in the 30–70 ° C. range.

VII. Keratinaceous Surfaces

In a living mammal, keratinaceous structures are derived from ectodermal (skin) cells and are generally free of vascularization. The essentially rigid keratinaceous structures such as nail plates and hooves are easily distinguished from hair, wool, skin, scales, feathers, and other relatively soft structures containing keratin as well as from other rigid but living tissue material such as tooth enamel or bone (which are not keratinaceous). For example, the class of keratins known as "alpha" keratin, which is characterized by a relatively large amount of cystine units, is a major constituent of nail plates and hooves. The essentially rigid keratinaceous structures of greatest interest in this invention are nail plates (fingernails and toenails, especially fingernails), which are quite commonly reshaped with the aid of acrylic ester monomers and polymers. Both the nail plate and surrounding skin areas can come into contact with the reshaping material, and the possibility that toxic substances in the reshaping material can be transported through both skin and nail plates is a matter of concern to public health officials. As explained previously, another concern is that materials which discolor upon exposure to light can adversely affect the quality of the reshaped nail plate. The curable compositions of this invention are formulated with a view toward avoiding both of these drawbacks.

The invention is illustrated by the following, non-limiting class of Part A/Part B formulations, wherein the weight-basis percentages apply to each part individually.

Part A:

>75% by weight, preferably 90 to 99.5% by weight polymerized acrylic ester powder, preferably ethyl methacrylate or methyl methacrylate homopolymer or ethyl/methyl methacrylate copolymer powder or mixture of all three types of polymers containing 0.5 to 10% by weight, preferably 1 to 5% by weight, an encapsulated barbituric acid derivative; 0.1 to 50 parts per million, preferably 0.1 to 10 ppm, of copper (II) acetyl acetonate. <25% by weight, preferably 0 to 5% by weight, optional ingredients (e.g. solvent).

The copper (II) acetyl acetonate, which is a solid, is uniformly distributed through the ethyl methacrylate, methyl methacrylate, or ethyl/methylmethacrylate copolymer or mixture of all three polymers powder.

Part B:

>75%, preferably 85 to 99.5% by weight, acrylic ester monomer, preferably ethyl methacrylate monomer; 0.1 to 2%, preferably 0.3 to 1%, of a quaternary ammonium salt, preferably dilauryldimethylammonium chloride; 0 to 20% by weight, preferably 1 to 15% by weight, of the crosslinker, preferably ethylene glycol dimethacrylate.

No solvent is added to Part B; the ethyl methacrylate is used as a reactive diluent or solvent. The quaternary ammonium salt, the ethylene glycol dimethacrylate and ethyl methacrylate monomer form an essentially clear solution.

Light Stability Test:

Using an artist's paint brush, the tip of the brush is first dipped in Part B and then in Part A. A ball-like, doughy mass of wetted powder is formed on the end of the brush. The doughy mass is then sculpted, for test purposes, on a release liner and permitted to cure to form a solid, essentially colorless poly(ethyl methacrylate) layer. After extensive weatherometer testing, using wavelengths in the range of 350 to 700 nm, no discoloration of the poly(ethyl methacrylate) layer can be observed.

All the references described above are incorporated by reference in its entireties for all useful purposes.

While there is shown and described herein certain specific structures embodying the invention, it will be manifest to those skilled in the art that various modifications and rearrangements of the parts may be made without departing from the spirit and scope of the underlying inventive concept and that the same is not limited to the particular forms herein shown and described.

What is claimed is:

1. A method for reshaping a nail plate surface comprising the step of applying, in vivo, to said nail plate surface a curable composition comprising an acrylic ester polymer and an acrylic ester monomer, said polymer contains a metal salt co-catalyst blended in with said polymer and an initiating amount of an initiator for the cure thereof, said initiator in the polymer matrix, wherein said initiator includes (a) said metal salt cocatalyst or a photoinitiator, other than a barbituric acid derivative or a barbituric acid salt, and (b) an encapsulated compound of the formula III

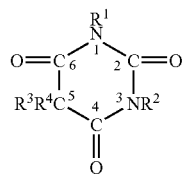

(III)

wherein $R^1$ through $R^4$ are identical to or different from each other and are hydrogen, a mononuclear carbocyclic aromatic group, a $C_1-C_{18}$ aliphatic group, a $C_1-C_{18}$ aliphatic radical substituted with a mononuclear carbocyclic aromatic group, a cycloaliphatic group or an aromatic radical having from 6 to 10 ring carbon atoms and up to five aliphatic or oxy- or oxo-aliphatic substituents, with the proviso that at least $R^3$ or $R^4$ is hydrogen, said curable composition being essentially free of aromatic amine, inorganic pigment, and particulate inorganic filler material.

2. The method according to claim 1, wherein $R^1$ and $R^2$ are the same or different and are hydrogen, $C_1-C_4$-alkyl, benzyl, phenethylene, or a mononuclear carbocyclic aromatic group, and $R^3$ is $C_1-C_4$-alkyl, benzyl, phenethylene, or a mononuclear carbocyclic aromatic group.

3. The method according to claim 2, wherein $R^2$ is hydrogen and $R^1$ and $R^3$ are the same or different and are $C_1-C_4$-alkyl, benzyl, phenethylene, or a monocyclic, carbocyclic aromatic group and $R^4$ is hydrogen.

4. The method according to claim 3, wherein $R^3$ is $C_1-C_4$-alkyl, phenyl, or benzyl.

5. The method according to claim 4, wherein $R^1$ is different from $R^3$ and is $C_1-C_4$-alkyl, phenyl, or benzyl and the composition contains less than about 2 weight % of benzyl peroxide.

6. The method according to claim 1, wherein said acrylic ester polymer is a powder and which comprises:

combining said acrylic ester polymer powder which has uniformly distributed and said encapsulated compound of the formula III, and a distributed uniformly there through, a metal salt co-catalyst, and applying the resulting combination to the nail plate surface.

7. The method according to claim 1, wherein said metal salt comprises a copper (II) salt of an organic diketone and said organic diketone is 2,4 pentanedione, napththenoate or acetylacetonate.

8. The method according to claim 7, wherein said organic diketone is 2,4 pentanedione.

9. The method according to claim 6, wherein said composition is cured with the aid of said initiator to form a laminar prosthesis on said nail plate surface.

10. The method according to claim 1, comprising:

a. applying a radiation-curable composition comprising said acrylic ester polymer, said photoinitiator, a photosensitizing compound which is capable of initiating a free-radical cure of said acrylic ester polymer when irradiated with light having a wavelength of at least about 400 nm, and, optionally, an aliphatic amine accelerator, and b. exposing said surface, to which said radiation-curable composition has been applied, to light having essentially a wavelength of at least about 400 nm.

11. A method of forming a laminar poly(acrylic ester) prosthesis in place, in vivo, on a human nail plate surface, comprising the step of applying to said human nail plate surface a combined part A/part B composition comprising:

said part A is 1. a powdery mass comprising a poly(acrylic ester)

2. an encapsulated compound of the formula III

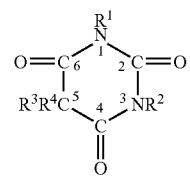

(III)

wherein $R^1$ through $R^4$ are identical to or different from each other and are hydrogen, a mononuclear carbocyclic aromatic group, a $C_1-C_{18}$ aliphatic group, a $C_1-C_{18}$ aliphatic radical substituted with a mononuclear carbocyclic aromatic group, a cycloaliphatic group or an aromatic radical having from 6 to 10 ring carbon atoms and up to five aliphatic or oxy- or oxo-aliphatic substituents, with the proviso that at least $R^3$ or $R^4$ is hydrogen, and 3. a metal salt, the metal of said metal salt having a plurality of oxidation states which differ from each other in electrochemical potential by less than about a volt, and said part B is 1. a liquid acrylic ester monomer composition which is essentially free of aromatic tertiary amine, 2. optionally, an organic ammonium compound and 3. a crosslinking compound;

said parts A and B having been kept separate from each other until combined for said applying step.

12. The method according to claim 11, wherein: the compound of formula III in said part A is a barbituric acid derivative in which $R^1$ and $R^2$ are identical to or different from each other and are hydrogen, a mononuclear carbocyclic aromatic group, a $C_1-C_6$ aliphatic group, a $C_1-C_6$ aliphatic radical substituted with a mononuclear carbocyclic aromatic group, or a cycloaliphatic group, and $R^3$, independently of $R^2$ and $R^3$ is a mononuclear carbocyclic aromatic group, a $C_1-C_{0.6}$ aliphatic group, a $C_1-C_{0.6}$ aliphatic radical substituted with a mononuclear carbocyclic aromatic group, or a cycloaliphatic group and $R^4$ is hydrogen.

13. The method according to claim 11, wherein, at least one of said $R^1$ and $R^2$ groups is a benzyl radical.

14. The method according to claim 11, wherein said part A contain a free radical-initiating amount of organic peroxide, which amount does not exceed 2 weight percent, based on the weight of said powder component.

15. A cured laminar poly (acrylic ester) prosthesis comprising cured parts A and B which have been cured by combining parts A and B:

said part A is
1. a powdery mass comprising a poly(acrylic ester)
2. an encapsulated compound of the formula III

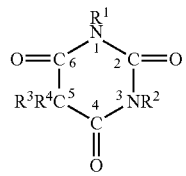
(III)

wherein $R^1$ through $R^4$ are identical to or different from each other and are hydrogen, a mononuclear carbocyclic aromatic group, a $C_1$–$C_{18}$ aliphatic group, a $C_1$–$C_{18}$ aliphatic radical substituted with a mononuclear carbocyclic aromatic group, a cycloaliphatic group or an aromatic radical having from 6 to 10 ring carbon atoms and up to five aliphatic or oxy- or oxo-aliphatic substituents, with the proviso that at least $R^3$ or $R^4$ is hydrogen, and
3. a metal salt, the metal of said metal salt having a plurality of oxidation states which differ from each other in electrochemical potential by less than about a volt and said part B is
1. a liquid acrylic ester monomer composition which is essentially free of aromatic tertiary amine,
2. optionally, an organic ammonium compound and a
3. crosslinking compound;

said parts A and B having been kept separate from each other until combined for said applying step.

16. A separately-packaged two-part system for forming, upon mixing of the two parts, a nail plate prosthesis in place on a nail plate, said two separately packaged parts, part A and part B, consisting essentially of:

part A consisting essentially of:
1. a powdery mass consisting essentially of at least one poly(acrylic ester)
2. an encapsulated compound of the formula III

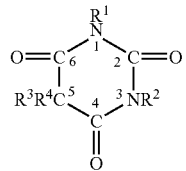
(III)

wherein $R^1$ through $R^4$ are identical to or different from each other and are hydrogen, a mononuclear carbocyclic aromatic group, a $C_1$–$C_{18}$ aliphatic group, a $C_1$–$C_{18}$ aliphatic radical substituted with a mononuclear carbocyclic aromatic group, a cycloaliphatic group or an aromatic radical having from 6 to 10 ring carbon atoms and up to five aliphatic or oxy- or oxo-aliphatic substituents, with the proviso that at least $R^3$ or $R^4$ is hydrogen, and said part A being essentially free of aromatic or aliphatic acyl peroxide; and 3. co-catalyst for said part A, said co-catalyst comprising a metal salt, part B consisting essentially of:
1. a liquid acrylic ester monomer consisting essentially of the ester and, an organic ammonium compound of the formula IV $R^5R^6R^7R^8N^+X^-$ (IV), where $R^5$, $R^6$, $R^7$, and $R^8$ are identical to or different from each other and are $C_1$–$C_{30}$-aliphatic or $C_{0.3}$–$C_{12}$-cycloaliphatic; and X is halide, alkylsulfonate, aryl sulfonate, alkyl phosphonate, aryl phosphonate, or one equivalent of sulfate or phosphate per equivalent of nitrogen;
2. optionally, a crosslinker;

said part B being essentially free of aromatic tertiary amine.

17. A kit for forming a nail plate prosthesis in place on a nail plate, said kit comprising said two-part system according to claim 16 and a shaping tool adapted to shape a mixture of the two parts of said two-part system.

18. A separately-packaged two-part system for forming, upon mixing of the two parts, a nail plate prosthesis in place on a nail plate, said two separately packaged parts, part A and part B, consisting essentially of:

part A consisting essentially of:
1. a powdery mass consisting essentially of at least one poly(acrylic ester)
2. an encapsulated compound of the formula III

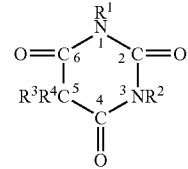
(III)

wherein $R^1$ through $R^4$ are identical to or different from each other and are hydrogen, a mononuclear carbocyclic aromatic group, a $C_1$–$C_{18}$ aliphatic group, a $C_1$–$C_{18}$ aliphatic radical substituted with a mononuclear carbocyclic aromatic group, a cycloaliphatic group or an aromatic radical having from 6 to 10 ring carbon atoms and up to five aliphatic or oxy- or oxo-aliphatic substituents, with the proviso that $R^3$ or $R^4$ is hydrogen, and
3. a co-catalyst comprising a metal salt, part B consisting essentially of:
1. a liquid acrylic ester monomer consisting essentially of ester and an organic ammonium compound of the formula IV $R^5R^6R^7R^8N^+X^-$ (IV), where $R^5$, $R^6$, $R^7$, and $R^8$ are identical to or different from each other and are $C_{0.1}$–$C_{30}$-aliphatic or $C_3$–$C_{12}$-cycloaliphatic; and X is halide, alkylsulfonate, aryl sulfonate, alkyl phosphonate, aryl phosphonate, or one equivalent of sulfate or phosphate per equivalent of nitrogen;
2. optionally, a cross linker;

said part B being essentially free of aromatic tertiary amine.

19. A separately-packaged two-part system for forming, upon mixing of the two parts, a nail plate prosthesis in place on a nail plate, said two separately packaged parts, part A and part B, consisting essentially of: part A: a powdery mass consisting essentially of at least one poly(acrylic ester) with an encapsulated compound of the formula III

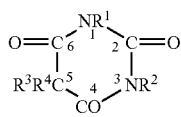

(III)

wherein $R^1$ through $R^4$ are identical to or different from each other and are hydrogen, a mononuclear carbocyclic aromatic group, a $C_1$–$C_{18}$ aliphatic group, a $C_1$–$C_{18}$ aliphatic radical substituted with a mononuclear carbocyclic aromatic group, a cycloaliphatic group or an aromatic radical having from 6 to 10 ring carbon atoms and up to five aliphatic or oxy- or oxo-aliphatic substituents, with the proviso that at least $R^3$ or $R^4$ is hydrogen and said part A contains less than about 2 weight % of co catalyst, part B: a liquid acrylic ester monomer consisting essentially ester and optionally, an organic ammonium compound of the formula IV $R^5R^6R^7R^8N^+X^-$ (IV), where $R^5$, $R^6$, $R^7$, and $R^8$ are identical to or different from each other and are $C_1$–$C_{30}$-aliphatic or $C_3$–$C_{12}$-cycloaliphatic; and X is halide, alkylsulfonate, aryl sulfonate, alkyl phosphonate, aryl phosphonate, or one equivalent of sulfate or phosphate per equivalent of nitrogen;

optionally, a crosslinker;

said part B being essentially free of aromatic tertiary amine.

20. A method for reshaping a nail plate surface comprising the step of applying to said nail plate a composition which comprises a part A and a part B, said part A and said part B comprising:

said part A is a polymerized acrylic ester powder component having, uniformly distributed, an encapsulated compound of formula III,

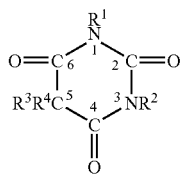

(III)

wherein $R^1$ through $R^4$ are identical to or different from each other and are hydrogen, a mononuclear carbocyclic aromatic group, a $C_1$–$C_{18}$ aliphatic group, a $C_1$–$C_{18}$ aliphatic radical substituted with a mononuclear carbocyclic aromatic group, a cycloaliphatic group or an aromatic radical having from 6 to 10 ring carbon atoms and up to five aliphatic or oxy- or oxo-aliphatic substituents, with the proviso that at least $R^3$ or $R^4$ is hydrogen, and a co-catalyst consisting essentially of a copper (II) salt of an organic diketone and being essentially free of aromatic tertiary amine; and, uniformly distributed through said polymerized acrylic ester powder component, said part B is a liquid acrylic ester monomer; uniformly distributed through said liquid acrylic ester monomer, a compound of the formula IV

$R^5R^6R^7R^8N^+X^-$ (IV)

where $R^5$, $R^6$, $R^7$, and $R^8$ are identical to or different from each other and are hydrogen, $C_1$–$C_{30}$-aliphatic, $C_3$–$C_{12}$-cycloaliphatic, or aromatic, but not more than 2 of said $R^5$, $R^6$, $R^7$, and $R^8$ are hydrogen; X is halide, alkylsulfonate, aryl sulfonate, alkyl phosphonate, aryl phosphonate, or one equivalent of sulfate or phosphate per equivalent of nitrogen, and said organic diketone is 2,4 pentanedione, napththenoate or acetylacetonate.

21. A method for reshaping a nail plate surface comprising combining (a) (i) a Polymerized acrylic ester powder component encapsulating (ii) a compound of the formula III and (iii) a uniformly distributed there through a metal salt co-catalyst with (b) an acrylic ester monomer component containing an amine buffer, and the resulting combination is applied to the nail plate surface and wherein said formula (Ill) is

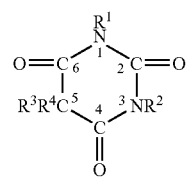

(III)

wherein $R^1$ through $R^4$ are identical to or different from each other and are hydrogen, a mononuclear carbocyclic aromatic group, a $C_1$–$C_{18}$ aliphatic group, a $C_1$–$C_{15}$ aliphatic radical substituted with a mononuclear carbocyclic aromatic group, a cycloaliphatic group or an aromatic radical having from 6 to 10 ring carbon atoms and up to five aliphatic or oxy- or oxo-aliphatic substituents, with the proviso that at least $R^3$ or $R^4$ is hydrogen, and said amine buffer is of the formula (IV)

$R^5R^6R^7R^8N^+X^-$ (IV)

where $R^5$, $R^6$, $R^7$, and $R^8$ are identical to or different from each other and are hydrogen, $C_1$–$C_3$-aliphatic, $C_3$–$C_{12}$-cycloaliphatic, or aromatic, but not more than 2 of said $R^5$, $R^6$, $R^7$, and $R^8$ are hydrogen; X is halide, alkylsulfonate, aryl sulfonate, alkyl phosphonate, aryl phosphonate, or one equivalent of sulfate or phosphate per equivalent of nitrogen.

* * * * *